United States Patent [19]
Hivale et al.

[11] Patent Number: 5,088,990
[45] Date of Patent: Feb. 18, 1992

[54] I.V. ALERT SYSTEM

[76] Inventors: Ronald S. Hivale; Almary M. Hivale, both of 192 Valley View Dr., Paradise, Calif. 95969

[21] Appl. No.: 400,885

[22] Filed: Aug. 30, 1989

[51] Int. Cl.$^5$ ............................................... A61M 5/14
[52] U.S. Cl. .................................... 604/253; 604/251; 604/67
[58] Field of Search .............. 604/67, 250, 251, 252, 604/253, 254; 340/573

[56] References Cited

U.S. PATENT DOCUMENTS

| | | | |
|---|---|---|---|
| 3,802,417 | 4/1974 | Lang | 340/573 X |
| 4,280,495 | 7/1981 | Lampert | 604/67 |
| 4,681,563 | 7/1987 | Deckert et al. | 604/67 |
| 4,681,569 | 7/1987 | Coble et al. | 604/253 |
| 4,827,970 | 5/1989 | Sugisaki et al. | 604/253 X |

OTHER PUBLICATIONS

Schilling, Donald L, et al., Electronic Circuits, Discrete and Integrated, 2nd ed., McGraw-Hill, copyright 1979.
IEEE Standard Dictionary of Electrical and Electronic Terms, [copyright 1972], p. 412.

Primary Examiner—Richard J. Apley
Assistant Examiner—L. Thomas
Attorney, Agent, or Firm—Richard C. Litman

[57] ABSTRACT

An intravenous alert system that uses CMOS circuitry. An infrared transmitter and receiver detects drops as they fall through a drip chamber. Each passing drop retriggers a counter. If the counter is not retriggered after a certain set delay time an alarm signal is sent out. The device uses both audio and visual alarms. A special adjustable housing contains all of the electronic components of the alert system.

10 Claims, 2 Drawing Sheets

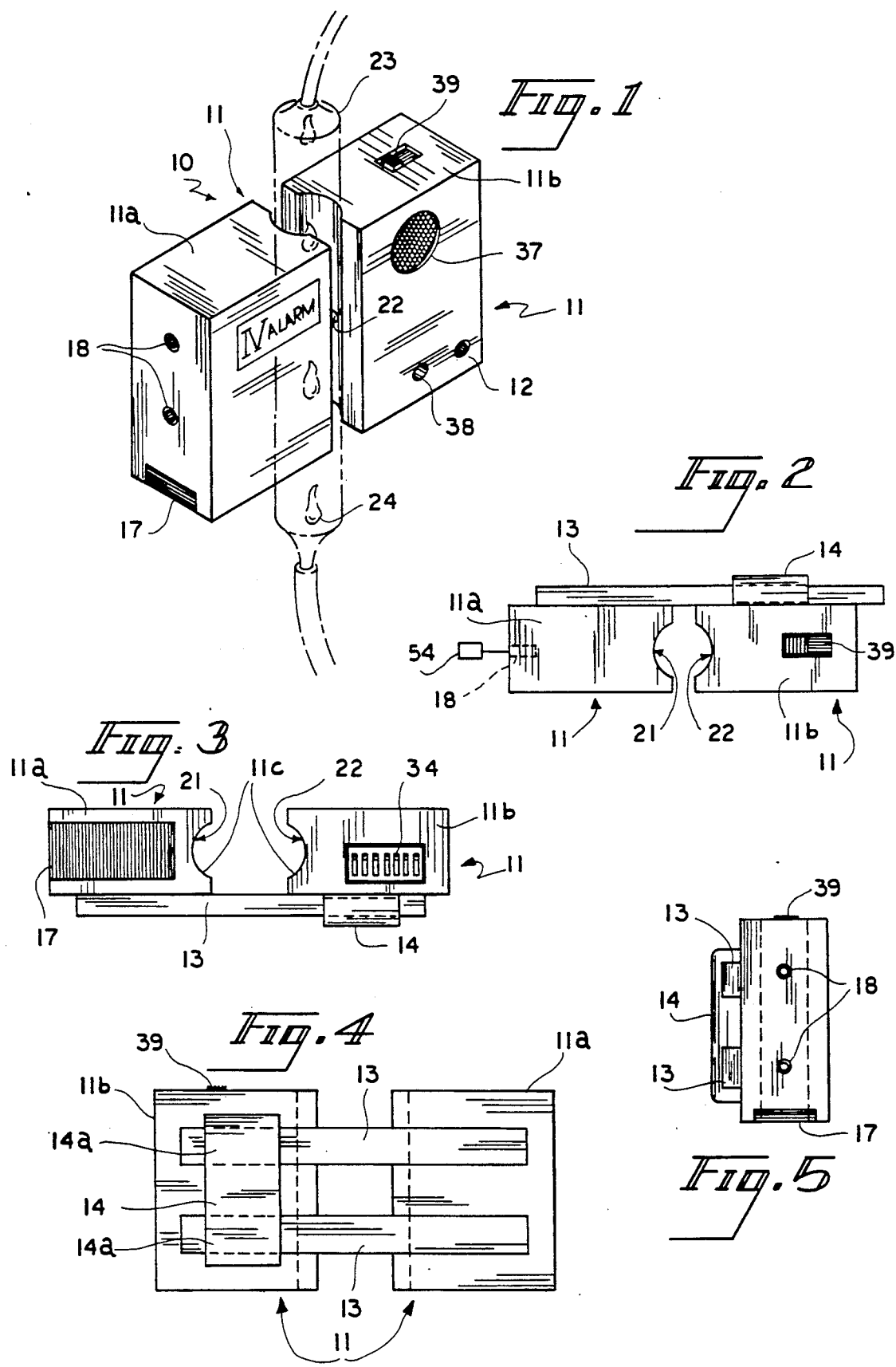

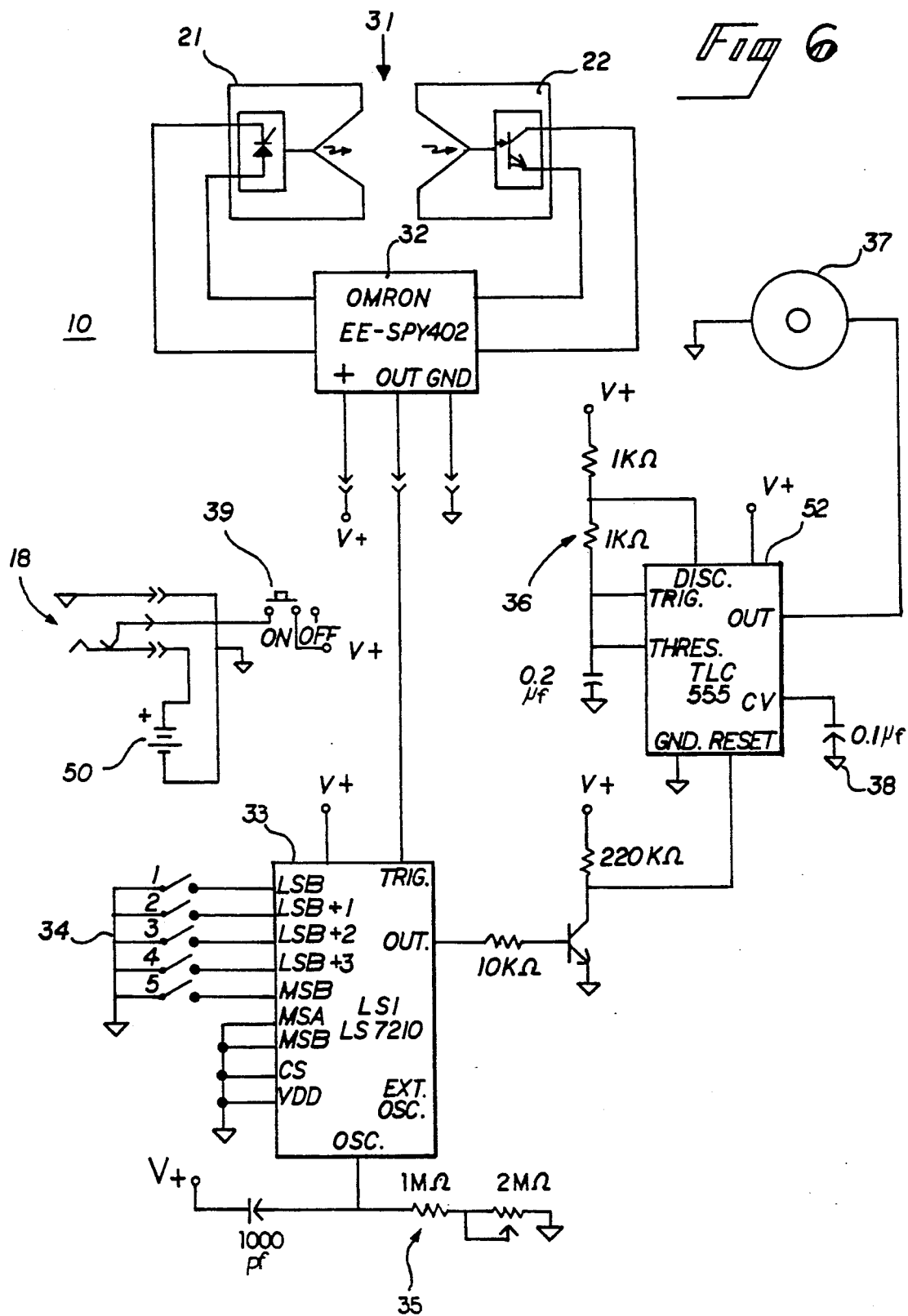

I.V. ALERT SYSTEM

BACKGROUND OF THE INVENTION

1. Field of the Invention

The present invention relates to the field of alarm devices using CMOS (Complimentary Metal Oxide Semiconductor) digital circuitry. More specifically it is a drip I.V. alarm used to alert the user that an intravenous infusion therapy has been completed. The invention has photovoltaic cells to detect each drop in an I.V. chamber. Each successive drop retriggers a counter. A long pause after a drop will set off alarm circuitry to warn of the completed I.V. infusion.

2. Description of the Prior Art

The following is a discussion of patents felt to be related in the field of the present invention, but do not disclose, whether singly or in combination, the applicants' unique construction.

Stephen Coble U.S. Pat. No. 4,681,569 discloses a battery-operated rate meter used for monitoring the fluid flow of an intravenous feeding system which comprises a housing having light emitters positioned opposite one another about the base of the drip chamber. The said rate meter calculates the passage of drops using photo-detecting properties therein and displays the detected input through LED indicator means.

Walter Jinotti U.S. Pat. No. 4,014,010 discloses a device similar to the patent described above in that the intravenous system flow meter comprising light detector means and electronic circuitry therein is used in combination with an alarm circuit having audio signaling means to warn the operator of fluid flow dripping below the set level.

SUMMARY OF THE INVENTION

The present invention is a small, portable I.V. alarm system. The alarm circuitry consists of CMOS digital electronics. The detector comprises an infrared photocell chamber having an emitter side and a receiver side. The emitter and receiver are positioned on either side of an I.V. drip chamber. Drops that pass through the emitter beam interrupt the constant voltage sent by the receiver. A voltage comparator sends a signal to trigger a counter, which counts up to a certain set delay time. If the counter is not retriggered by another drop at the end of the counting sequence, an alarm oscillator is set in action to operate an alarm buzzer and a visible LED (Light Emitting Diode). The device can be set in terms of the length of allowable time delay for the counter and the alarm can be turned off after an initial signal to reset the system as a whole.

Accordingly, it is an object of the present invention to provide a portable I.V. drip alarm system.

Another object of the present invention is to provide an I.V. alarm system using CMOS circuitry.

It is a further object of the present invention to provide an I.V. alarm system using infrared photovoltaic cells.

It is still another object of the present invention to provide an I.V. alarm system with an user-adjustable timing circuit.

These and other objects of the present invention will readily become apparent upon review of the attached drawings and specification.

BRIEF DESCRIPTION OF THE DRAWINGS

FIG. 1 shows a perspective view of the portable I.V. alarm system with the drip chamber in outline.

FIG. 2 shows a top view of the I.V. alert system.

FIG. 3 shows a bottom view of the I.V. alert system.

FIG. 4 shows a rear view of the I.V. alert system.

FIG. 5 shows a side view of the I.V. alert system.

FIG. 6 shows a circuit diagram for the I.V. alert system.

Similar reference characters denote corresponding parts throughout the drawings.

DESCRIPTION OF THE PREFERRED EMBODIMENT

FIG. 1 shows the packaged alarm system 10 having a plastic casing 11, reset switch 12, alarm speaker 37 and an LED indicator 38. The system has two separate housing or containment sections 11a and 11b that are placed on either side of an I.V. drip chamber 23. A plurality of arms 13 slide through a bracket 14 having separate passages 14a for each arm 13, as shown in FIG. 4, allowing the width of the gap between the channels 11c,11c on the two sections 11a, 11b to be adjusted in order to accommodate different sized drip chambers 23. The whole outer housing assembly 11 can be constructed from a relatively soft, resilient plastic which would allow arms 13 and brackets 14 to have an easily slidable friction fit.

Recharger contacts 18 and battery door 17, shown in FIGS. 3 and 5, are provided on the side and on the bottom of housing section 11a. Also included on the housing 11 are 5 or more DIP (Dual Inline Package) switches 34 that adjust the alert period between drops 24 in the drip chamber 23, and an on-off switch 39. To connect the various components in the two housings 11a,11b a connecting line (not shown) would be sent through or adjacent to the arm 13 and bracket 14 assembly. The alarm system 10 is small enough to fit within a normal shirt pocket, being no more than 4 inches by $2\frac{1}{8}$ inches by $\frac{7}{8}$ inches thick.

The photovoltaic cell is shown in FIGS. 1, 2, 3 and 6. The cell consists of a singular emitter 21 and receiver 22 spaced opposite each other in the channels 11c of sections 11a and 11b. The specific device used to emit is an infrared diode 21 which emits a beam of infrared light through a clear I.V. drip chamber 23 to an infrared detector 22. The advantage of using infrared light instead of visible light is that there will be less interference from the outside visible light sources around the device.

The receiver 22 receives a constant signal from the emitter 21 until a drop 24 intercepts the path between emitter 21 and receiver 22. The interposing of the drop 24 between the emitter diode 21 and the receiver 22 changes the receiver's incoming signal. The receiver 22 is constantly sending out a signal to the alarm circuitry. This receiver output is changed accordingly and causes a reaction in the alarm circuitry as will be detailed below.

The alarm circuitry contains a power source for the whole device. Nickel-cadmium batteries 50 of 7.2 volt type are used because of their long life. These types of batteries 50 are also easily rechargeable, hence the recharging ports 18 consisting of a common DC port connectable to a conventional battery recharger 54 which is operable to recharge batteries 50 only when on-off switch 59 is in the off position and the alarm system is not being used, as is well known in the battery recharging art. These batteries 50 should keep the alarm device functional for about 5 hours as the device has low power requirements with CMOS circuitry.

FIG. 6 shows the circuit diagram for the device. Sensor block 31 consists of an emitter and receiver 21,22. A voltage comparator 32 is constantly checking for voltage fluctuations. If it detects one, a signal pulse is sent to a counter 33 (4541 type) which begins a counting sequence. Should another pulse be sent by the comparator 32, the counter 33 will be retriggered to start at the beginning. A five-position DIP switch 34, a)so shown in FIG. 3, allows the user to set the maximum drop delay time for the counter 33. Should the counter 33 reach this maximum delay count without being retriggered by a comparator pulse, the counter 33 outputs a pulse to an AF (Audio Frequency, ½ 556C type) oscillator 35, which will in turn output a pulse to an astable modulating oscillator (½ 556C type) 36. The modulating oscillator 36 is connected to a Piezo audio transducer or speaker 37 which produces the alarm sound. The two oscillators 35, 36 are capable of producing a variety of sounds. A modulated single tone (on-off-on-off), a modulated dual tone (high-low-high-low) or an unmodulated single tone. The type of tone can be selected by the user of the device 10.

A low power visual alarm LED 38 is connected to the output of another CMOS timer/multivibrator 52 (555C type) similar to oscillator 36 which is also controlled by the reset pulse of the drip sensing comparator 32. Oscillator timings of 100 ms are good for viewing. Reset switch 12 would send a pulse back to the counter 33 to retrigger its sequence separately of the voltage comparator 32.

In use the maximum desired delay time is about 20 seconds. The five-position DIP switch 34 can select a range between 20 seconds and zero time between drops in the I.V. chamber 23. The DIP switch 34 could have a variable amount of positions. Five are taken as a good sampling of drip times.

It is to be understood that the present invention is not limited to the sole embodiment described above, but encompasses any and all embodiments within the scope of the following claims.

We claim:

1. An intravenous alert system comprising:
    infrared photovoltaic sensing means, placed on either side of an intravenous drip chamber to detect drops as they pass by;
    comparator means to detect a change in an output voltage that is sent by said drop sensing means, said comparator means sending a trigger signal when said drop sensing means detects a drop;
    counter means to time the interval between drops in said drip chamber, said counter means receiving and being restarted by each new trigger signal from said comparator means. said counter means sending a signal when said counter means reaches a predetermined value;
    audio frequency oscillator means to receive said signal from said counter means, said audio frequency oscillator means sending out an audio frequency oscillator signal upon receiving said signal from said counter means;
    astable modulating oscillator means to receive said audio frequency oscillator signal from said audio frequency oscillator means, said astable modulating oscillator means sending an astable modulated oscillator signal;
    audio alarm means to receive said astable modulated oscillator signal and to signal discontinuance of intravenous dripping;
    containment means for said drop sensing means, comparator means, counter means, audio frequency oscillator means, astable modulating oscillator means and said alarm means;
    power means to provide current to said intravenous alert system;
    switch means to switch said power means on or off; and
    CMOS circuitry being used to construct said comparator means, counter means, audio frequency oscillator means and astable modulating oscillator means, said CMOS circuitry providing a small size to the intravenous alert system allowing ease of use and portability.

2. The intravenous alert system according to claim 1, including:
    recharger means connected to said power means; when said power means is switched off by said switch means, to recharge said power means.

3. The intravenous alert system according to claim 1, wherein:
    said infrared photovaltaic drop sensing means comprises an infrared emitter and an infrared receiver.

4. The intravenous alert system according to claim 1, including:
    visual alarm means connected to said astable, modulating oscillator means.

5. The intravenous alert system according to claim 1, wherein:
    said predetermined value is able to be varied by a means to vary operable by the user of said intravenous alert system.

6. The intravenous alert system according to claim 5, wherein:
    said means to vary said predetermined value are a series of DIP switches located on said containment means.

7. The intravenous alert system according to claim 1, wherein:
    said audio alarm means is a piezo audio transducer.

8. The intravenous alert system according to claim 4, wherein:
    said visual alarm means is an LED.

9. The intravenous alert system according to claim 1, wherein:
    said containment means comprises two separate sections disposed on opposite sides of said drip chamber, said sections are connected by at least one elongated arm on one of said sections being disposed through a receiving slot on the other of said sections, said arm and slot being laterally offset from said sections and said drip chamber and having a sliding adjustable fit to accommodate various sized drip chambers.

10. The intravenous alert system according to claim 9, wherein:
    each said section has a semi-cylindrical channel on a side of each said section, said semi-cylindrical channels are disposed opposite each other such that an I.V. drip chamber can be disposed therebetween.

* * * * *